United States Patent
Kikuchi et al.

(10) Patent No.: US 8,318,958 B2
(45) Date of Patent: Nov. 27, 2012

(54) OXIDIZING AGENT COMPOSITION FOR EPOXIDATION AND OXIDATION METHOD THEREOF

(75) Inventors: Takaaki Kikuchi, Tokyo (JP); Takehiro Zushi, Tokyo (JP); Hirohisa Nitoh, Tokyo (JP)

(73) Assignee: Adeka Corporation, Tokyo (JP)

( * ) Notice: Subject to any disclaimer, the term of this patent is extended or adjusted under 35 U.S.C. 154(b) by 300 days.

(21) Appl. No.: 12/733,847

(22) PCT Filed: Sep. 26, 2008

(86) PCT No.: PCT/JP2008/067454
§ 371 (c)(1),
(2), (4) Date: Mar. 24, 2010

(87) PCT Pub. No.: WO2009/041592
PCT Pub. Date: Apr. 2, 2009

(65) Prior Publication Data
US 2010/0228040 A1    Sep. 9, 2010

(30) Foreign Application Priority Data
Sep. 26, 2007  (JP) .................. 2007-249693

(51) Int. Cl.
*C07D 301/16*    (2006.01)
(52) U.S. Cl. ...................... 549/524; 549/525
(58) Field of Classification Search ........... 549/524, 549/525, 526
See application file for complete search history.

(56) References Cited

U.S. PATENT DOCUMENTS
4,590,286 A    5/1986    Bull

FOREIGN PATENT DOCUMENTS
| | | |
|---|---|---|
| CN | 1 422 853 | 6/2003 |
| CN | 101 003 522 | 7/2007 |
| JP | 62-106089 | 5/1987 |
| JP | 2007-145744 | 6/2007 |
| JP | 2008-173630 | 7/2008 |
| WO | 2006/043075 | 4/2006 |

OTHER PUBLICATIONS

International Search Report issued Oct. 28, 2008 in International (PCT) Application No. PCT/JP2008/067454.
Supplementary European Search Report dated Feb. 2, 2011 issued in Application No. EP 08833535.1.
F. Tao et al., "A New Reagent Pair Sodium Percarbonate-acetic Anhydride for Epoxidation of Olefins", Acta Chimica Sinica (English Edition), vol. 5, pp. 463-467, 1989.
G. Xie et al., "Sodium Perborate Oxidations of Cyclic and Acrylic Alkenes to Oxiranes or Vicinal Acetoxy Alcohols", Tetrahedron Letters, vol. 29, No. 24, pp. 2967-2968, 1988.
A. M. Rocha Gonsalves et al., "Dissociation of Hydrogen Peroxide Adducts in Solution: The Use of Such Adducts for Epoxidation of Alkenes", Journal of Chemical Research, pp. 208-209, Jan. 1, 1991.

*Primary Examiner* — Bernard Dentz
(74) *Attorney, Agent, or Firm* — Wenderoth, Lind & Ponack, L.L.P.

(57) ABSTRACT

Disclosed is a method for epoxidizing olefins, which enables an epoxy compound containing no halogen atom with high yield. Specifically disclosed is an oxidizing agent composition for epoxidation of olefins, which is characterized by containing peroxide which exhibits basicity when dissolved in water and an acid anhydride.

4 Claims, No Drawings

OXIDIZING AGENT COMPOSITION FOR EPOXIDATION AND OXIDATION METHOD THEREOF

This application is a U.S. national stage of International Application No. PCT/JP2008/067454 filed Sep. 26, 2008.

TECHNICAL FIELD

The present invention relates to an oxidizing agent composition for epoxidation which efficiently oxidizes a double bond contained in olefins and an oxidation method thereof.

BACKGROUND ART

Epoxy compounds have been used as raw materials in various fields such as resins, coatings, medicines, agricultural chemicals, and electronic materials, and there are several methods of producing the epoxy compounds. Of these, the method which has been most generally carried out is a method involving reacting epichlorohydrin or the like with alcohols (for example, see Patent Document 1). These epoxy compounds contain impurities, but are cheap and suitable for mass production, and thus are used in many fields. However, not all of the halogen atoms derived from the raw material can be removed from these epoxy compounds, so from the viewpoint of the dioxin problem or the like, an epoxy compound which does not have a halogen atom has been sought.

In addition, as another method, there is a method involving using peroxide compounds such as hydrogen peroxide and peracetic acid or the like (for example, see Patent Documents 2 and 3). When these oxidizing agents are used, the incorporation of a halogen atom can be avoided, but the yield is poor in all cases, and in particular, there has been a problem with the a large amount of glycols being generated as by-products.

Patent Document 1: JP 05-017463 A
Patent Document 2: JP 05-213919 A
Patent Document 3: JP 06-172335 A

DISCLOSURE OF THE INVENTION

Problem to be Solved by the Invention

Accordingly, a problem to be solved by the present invention is to provide a method of epoxidizing olefins, which enables the production of a halogen-free epoxy compound in high yield.

Means for Solving the Problem

The inventors of the present invention have extensively studied to find an oxidizing agent composition capable of efficiently performing an oxidation reaction, thereby achieving the present invention. That is, the present invention provides an oxidizing agent composition for epoxidation of olefins containing peroxide which exhibits basicity when dissolved in water and an acid anhydride.

Effect of the Invention

An effect of the present invention is that an oxidation method, which enables the production of a halogen-free epoxy compound in high yield, is provided.

BEST MODE FOR CARRYING OUT THE INVENTION

First, acid anhydrides which can be used in the present invention are described. The acid anhydrides can be broadly divided into two types in terms of their structures: an acid anhydride obtained by dehydration condensation of two molecules of carbonyl group-containing compounds; and an acid anhydride obtained by intramolecular dehydration condensation of a compound having two or more carbonyl groups in one molecule. In the present invention, both types of acid anhydrides can be used and can be represented by the following general formulae (1) and (2).

[Chem 1]

($R^1$ and $R^2$ each represent a hydrogen atom or a hydrocarbon group which may include an oxygen atom.)

[Chem 2]

($R^3$ represents a hydrocarbon group which may include an oxygen atom.)

Examples of the acid anhydride represented by the general formula (1) include acid anhydrides obtained by dehydration condensation of monocarboxylic acids such as formic acid, acetic acid, propionic acid, butanoic acid (butyric acid), pentanoic acid (valeric acid), isopentanoic acid (isovaleric acid), hexanoic acid (caproic acid), heptanoic acid, isoheptanoic acid, octanoic acid (caprylic acid), 2-ethylhexanoic acid, isooctanoic acid, nonanoic acid (pelargonic acid), isononanoic acid, decanoic acid (capric acid), isodecanoic acid, undecanoic acid, isoundecanoic acid, dodecanoic acid (lauric acid), isododecanoic acid, tridecanoic acid, isotridecanoic acid, tetradecanoic acid (myristic acid), hexadecanoic acid (palmitic acid), octadecanoic acid (stearic acid), isostearic acid, and oleic acid. The acid anhydride may be a dehydrated condensate of monocarboxylic acids of the same kind or may be a dehydrated condensate of monocarboxylic acids of different kinds. The dehydrated condensate of the monocarboxylic acids of the same kind is preferred because the dehydrated condensate is versatile and easily produced. Examples of the dehydrated condensate of the same kind of monocarboxylic acids include formic anhydride, acetic anhydride, propionic anhydride, butanoic anhydride, pentanoic anhydride, hexanoic anhydride, octanoic anhydride, decanoic anhydride, dodecanoic anhydride, and octadecanoic anhydride or the like. Of these, the acid anhydrides each having a small molecular weight in which $R^1$ and $R^2$ each represent a hydrogen atom or a hydrocarbon group having 1 to 4 carbon atoms are preferred, formic anhydride, acetic anhydride, and propionic anhydride are more preferred, and acetic anhydride is still more preferred because it is the most versatile and has high stability. When the molecular weight of the acid anhydride becomes larger, the amount of carboxylic acid per unit mass decreases and the blending amount of the acid anhydride increases, thus it may be economically disadvantageous, and when the molecular weight is large, the removal of the acid anhydride by water washing is difficult, thus purification after the completion of the reaction may become difficult.

Examples of the acid anhydride represented by the general formula (2) include succinic anhydride, maleic anhydride, phthalic anhydride, trimellitic anhydride, pyromellitic anhydride, and hydrogenated phthalic anhydride. For the same reason as described above, the acid anhydrides in which $R^3$ represents a hydrocarbon group having 2 to 6 carbon atoms are preferred, succinic anhydride, maleic anhydride, and phthalic anhydride are more preferred.

Next, the peroxide which exhibits basicity when dissolved in water is described. Examples of such peroxide include sodium percarbonate, potassium percarbonate, sodium perborate, potassium perborate, sodium peroxide, potassium peroxide, calcium peroxide, magnesium peroxide, lithium peroxide, barium peroxide, and cesium peroxide. Of these, a percarbonate or a perborate is preferred because of their high epoxidation effect, and still further, sodium percarbonate is more preferred because of its economic excellent value.

The oxidizing agent composition for epoxidation of the present invention contains the peroxide and the acid anhydride described above, and the blending ratio is preferably from 0.4 to 2 mol and more preferably from 0.5 to 1.2 mol of the peroxide to 1 mol of the acid anhydride. When the amount of the peroxide with respect to the acid anhydride is too large or too small, there may be a case where the oxidation reaction does not proceed smoothly.

Here, the reason for using the peroxide which exhibits basicity when dissolved in water is described. During epoxidation reaction of the present invention, when, for example, sodium percarbonate and acetic anhydride are used, sodium percarbonate acts on acetic anhydride to give acetic acid and peracetic acid, the generated peracetic acid acts on an olefin so that peracetic acid degrades to acetic acid, and the olefin is epoxidized. In this way, a fatty acid derived from the acid anhydride is generated as reaction a by-product. This fatty acid is a substance which acts disadvantageously on the epoxidation reaction or the generated epoxy compound by for example, exterting a harmful influence such as reacting with the generated epoxy compound to open an epoxy ring. However, as sodium percarbonate and the like exhibit basicity when dissolved in water, reaction inhibition is prevented because the fatty acid inhibiting the reaction is neutralized. Owe to this an epoxy compound with high purity can be obtained easily. On the other hand, although when a peroxide such as urea peroxide or the like which exhibits neutrality when dissolved in water is used instead of sodium percarbonate to epoxidize an inner olefin of dicyclopentadiene or the like, the epoxidation can be carried out with relatively high yield, as it is difficult for the generated epoxy compound to react with the fatty acid by-product, because the reactivity of the generated epoxy compound is low, when it is used to epoxidese an olefin having a double bond at the terminal or the like, as a highly reactive epoxy compound is generated, the epoxy compound reacts with a fatty acid by-product and the reaction rate becomes low. However, by using the oxidizing agent composition for epoxidation of the present invention, regardless of the kind of olefins to be used, even in the case of using an inner olefin or a terminal olefin, an epoxy compound with the same high purity can be obtained.

The olefins which can be used in the present invention may be terminal olefins or inner olefins as long as the olefins are each an organic compound having a double bond. The molecule thereof may have one double bond or two or more double bonds. With regard to olefins each having two or more inner olefins in one molecule and olefins each having one or more inner olefins and one or more terminal olefins in one molecule, as it is difficult for them to be epoxidized with existing oxidizing agents for epoxidation with these olefins are preferred as the olefins to be used with the oxidizing agent composition for epoxidation of the present invention. Further, substituents such as a hydroxyl group and a carbonyl group may be substituted for the olefins. In the present application, in the case where n double bond(s) is/are present in one olefin molecule, it is defined as n-equivalent olefin. That is, the olefin having one double bond is referred to as 1-equivalent olefin and the olefin having two double bonds is referred to as 2-equivalent olefin.

Examples of these olefins include: monoolefins such as 1-hexene, 1-decene, 1-dodecene, cyclohexene, oleyl alcohol, styrene, and allyl alcohol; diolefins such as divinylbenzene, dicyclopentadiene, and limonene; and other trifunctional or higher functional polyolefins. In general, it is more difficult to epoxidize a compound having two or more double bonds in the molecule or an inner olefin compared to a compound having one double bond in the molecule or a terminal olefin. However, the oxidizing agent composition of the present invention can easily epoxidize even these compounds without generating by-products, and further, even when the obtained epoxy compound is highly reactive, the epoxy compound does not react with other substances, and hence, the yield is not lowered.

The oxidation method of the present invention is a method involving mixing a peroxide which exhibits basicity when dissolved in water, an acid anhydride, and olefins and epoxidizing the double bonds of the olefins by oxidation. A solvent may be used or may not be used during the reaction. However, the mixture is preferably diluted with the solvent and then subjected to the reaction, because there is a case where the reaction does not proceed homogeneously when the reaction system becomes highly viscous or solid and it is easier to control reaction heat. Examples of the usable solvent include: alcohols such as methanol, ethanol, propanol, isopropanol, butanol, isobutanol, secondary butanol, tertiary butanol, pentanol, isopentanol, secondary pentanol, neopentanol, tertiary pentanol, hexanol, secondary hexanol, heptanol, secondary heptanol, octanol, and 2-ethylhexanol; aromatics such as benzene, toluene, and xylene; aliphatic hydrocarbons and alicyclic hydrocarbons such as hexane, heptane, decane, and cyclohexane; ester-based solvents such as ethyl acetate, propyl acetate, and butyl acetate; and water. Of these solvents, aromatics, aliphatic hydrocarbons, alicyclic hydrocarbons, and water are preferred, and toluene, xylene, hexane, and water are more preferred, because they are easily purified in the case where the purification by water washing is conducted after the completion of the reaction.

The peroxide which exhibits basicity when dissolved in water and the acid anhydride may be mixed at the same time or separately with the olefins.

The blending ratio of the oxidizing agent composition for epoxidation of the present invention when oxidizing the olefins is n mol or more, preferably n to 10n mol, and more preferably 2n to 6n mol of the peroxide to 1 mol of n-equivalent olefins. When the blending ratio of the peroxide is less than n mol, the epoxidation of the olefins does not proceed completely.

A reaction temperature is preferably 20 to 100° C., more preferably 40 to 80° C., and still more preferably 50 to 60° C. When the reaction temperature is lower than 20° C., the reaction rate becomes slow and there may be a case where the reaction is not completely finished, and when the reaction temperature exceeds 100° C., there may be a case where a peroxide rapidly decomposes which is dangerous. The reaction may be carried out by stirring the system for 1 to 30 hours and preferably 2 to 20 hours.

EXAMPLES

Hereinafter the present invention is described specifically by way of examples. Unless otherwise mentioned, "%" and "ppm" used in examples and the like below are each expressed in mass standard. "GC purity" mentioned in the following analysis means purity measured by gas chromatography. Measurement conditions are described below.
<Gas Chromatography Measurement Conditions>
Measuring instrument: GC-15A (manufactured by Shimadzu Corporation)
Column: DB-1 (15 m capillary column)
Detector: FID
Carrier gas: nitrogen gas, 1 kgf/cm$^2$
Injection temperature: 280° C.
Column temperature: 150 to 270° C. (temperature rise at a rate of 10° C./min)

Example 1

Limonene (1.36 g, 10 mmol) was dissolved in butyl acetate (25 ml), and a composition containing sodium percarbonate (10.5 g, 66.7 mmol) and acetic anhydride (10.2 g, 100 mmol) was added thereto. The mixture was stirred at 60° C. After 12 hours, the reaction solution was washed with water to thereby completely remove acetic acid and sodium acetate, which were generated as by-products, and the remaining $H_2O_2$. Butyl acetate was distilled off from the organic phase by distillation, and as a result, 1.66 g (99% yields) of limonene diepoxide with a GC purity of 100% was obtained.

Example 2

Limonene (1.36 g, 10 mmol) was dissolved in toluene (25 ml), and a composition containing sodium percarbonate (10.5 g, 66.7 mmol) and phthalic anhydride (14.8 g, 100 mmol) was added thereto. The mixture was stirred at 60° C. After 12 hours, the reaction solution was washed with water to thereby completely remove phthalic acid, sodium phthalate, and disodium phthalate, which were generated as by-products, and the remaining $H_2O_2$. Toluene was distilled off from the organic phase by distillation, and as a result, 1.66 g (99% yields) of limonene diepoxide with a GC purity of 100% was obtained.

Example 3

Limonene (1.36 g, 10 mmol) was dissolved in toluene (25 ml), and a composition containing sodium perborate tetrahydrate (15.4 g, 100 mmol) and acetic anhydride (10.2 g, 100 mmol) was added thereto. The mixture was stirred at 60° C. After 12 hours, the reaction solution was washed with water to thereby completely remove acetic acid and sodium acetate, which were generated as by-products, and the remaining $H_2O_2$. Toluene was distilled off from the organic phase by distillation, and as a result, 1.63 g (97% yields) of limonene diepoxide with a GC purity of 98% was obtained.

Example 4

Dicyclopentadiene (1.32 g, 10 mmol) was dissolved in toluene (25 ml), and a composition containing sodium percarbonate (10.5 g, 66.7 mmol) and acetic anhydride (10.2 g, 100 mmol) was added thereto. The mixture was stirred at 60° C. After 12 hours, the reaction solution was washed with water to thereby completely remove acetic acid and sodium acetate, which were generated as by-products, and the remaining $H_2O_2$. Toluene was distilled off from the organic phase by distillation, and as a result, 1.62 g (99% yields) of dicyclopentadiene diepoxide with a GC purity of 100% was obtained.

Example 5

1-Dodecene (1.68 g, 10 mmol) was dissolved in toluene (25 ml), and a composition containing sodium percarbonate (10.5 g, 66.7 mmol) and acetic anhydride (10.2 g, 100 mmol) was added thereto. The mixture was stirred at 60° C. After 12 hours, the reaction solution was washed with water to thereby completely remove acetic acid and sodium acetate, which were generated as by-products, and the remaining $H_2O_2$. Toluene was distilled off from the organic phase by distillation, and as a result, 1.82 g (99% yields) of 1-dodecene monoepoxide with a GC purity of 100% was obtained.

Example 6

Limonene (1.36 g, 10 mmol) was dissolved in butyl acetate (25 ml), and a composition containing sodium percarbonate (6.0 g, 38.1 mmol) and acetic anhydride (10.2 g, 100 mmol) was added thereto. The mixture was stirred at 60° C. After 12 hours, the reaction solution was washed with water to thereby completely remove acetic acid and sodium acetate, which were generated as by-products, and the remaining $H_2O_2$. Butyl acetate was distilled off from the organic phase by distillation, and as a result, 1.63 g (97% yields) of limonene diepoxide with a GC purity of 97% were obtained.

Comparative Example 1

A reaction was carried out in the same manner as the experiment method of Example 1 above, except that acetic acid (12 g, 200 mmol) was used instead of acetic anhydride, but the reaction did not proceed at all, and 99% of the raw material was collected.

Comparative Example 2

A reaction was carried out in the same manner as the experiment method of Example 1 above, except that 60% hydrogen peroxide (3.78 g, 66.7 mmol) was used instead of sodium percarbonate. The yield of limonene diepoxide was 78%, the yield of limonene diglycol (ring-opened product) was 18%, and 4% of limonene as the raw material was collected.

Comparative Example 3

A reaction was carried out in the same manner as the experiment method of Example 1 above, except that urea peroxide (6.3 g, 66.7 mmol) was used instead of sodium percarbonate. The yield of limonene diepoxide was 75%, the yield of limonene monoepoxide was 12%, and there was 13% of ring-opened product.

Comparative Example 4

A reaction was carried out in the same manner as the experiment method of Example 5 above, except that urea peroxide (6.3 g, 66.7 mmol) was used instead of sodium percarbonate. The yield of 1-dodecene monoepoxide was 50%, and there was 50% of ring-opened product.

INDUSTRIAL APPLICABILITY

When the present invention is used, a halogen-free epoxy compound can be obtained in high yield. Such an epoxy compound is useful in various fields such as resins, coatings, medicines, agricultural chemicals, and electronic materials.

The invention claimed is:

1. A method of epoxidizing an olefin, comprising reacting a percarbonate, an acid anhydride and an olefin in a solvent,
    wherein at least 6.67 mole of percarbonate with respect to 1 mole of olefin is reacted, and
    wherein the solvent is selected from the group consisting of methanol, ethanol, propanol, isopropanol, butanol, isobutanol, secondary butanol, tertiary butanol, pentanol, isopentanol, secondary pentanol, neopentanol, tertiary pentanol, hexanol, secondary hexanol, heptanol, secondary heptanol, octanol, 2-ethylhexanol, benzene, toluene, xylene, hexane, heptane, decane, cyclohexane, ethyl acetate, propyl acetate, butyl acetate, water and combinations thereof.

2. The method according to claim 1, wherein the acid anhydride is selected from the group consisting of formic anhydride, acetic anhydride, propionic anhydride, succinic anhydride, maleic anhydride, phthalic anhydride and combinations thereof.

3. The method according to claim 1, wherein the reaction is conducted under a temperature of between 40-80° C.

4. The method according to claim 2, wherein the reaction is conducted under a temperature of between 40-80° C.

* * * * *